(12) United States Patent
Lartey et al.

(10) Patent No.: US 6,872,388 B1
(45) Date of Patent: Mar. 29, 2005

(54) DEGRADATION OF CERCOSPORIN BY LACCASE

(75) Inventors: Robert T. Lartey, Sidney, MT (US); TheCan Caesar, Sidney, MT (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 240 days.

(21) Appl. No.: 10/205,871

(22) Filed: Jul. 26, 2002

(51) Int. Cl.$^7$ .................. A61K 35/70; A61K 38/44
(52) U.S. Cl. ............. 424/93.5; 424/405; 424/94.4; 504/117; 435/189; 435/420
(58) Field of Search ............... 424/93.5, 405, 424/94.4, 94.3; 504/117; 435/189, 420

(56) References Cited

U.S. PATENT DOCUMENTS 5,262,306 A    11/1993   Robeson et al.

FOREIGN PATENT DOCUMENTS

| EP | 1167528 A | * | 1/2002 |
| WO | WO 01/40442 | * | 6/2001 |

OTHER PUBLICATIONS

Curreli et al., "Effects of plant–derived naphthoquinones on the growth of Pleurotus sajor–caju and degradation of the compounds by fungal cultures," J Basic Microbiol 41(5):253–259, 2001.*

G.N. Odvody et al., Biological Control of *Rhizoctonia solani* with a Soil–Inhabiting Basidiomycete, The American Phytopathological Society, vol. 70, No. 7, pp. 655–658, 1980.

S.B. Martin et al., Influence of the Antagonist *Laetisaria arvalis* on Infection of Table Beets by *Phoma betae*, The American Phytopathological Society, vol. 74, No. 9, pp. 1092–1096, 1984.

H.J. Larsen, et al., Temporary Depression of *Rhizoctonia solani* Field Populations by Soil Amendment with *Laetisaria arvalis*, The American Phytopathological Society, vol. 69, No. 4, pp. 347–350, Plant Disease/Apr. 1985.

H.C. Hoch et al., Biological Control of Pythium Root Rot of Table Beet with *Corticium* sp., The American Phytopathological Society, vol. 69, No. 4, pp. 417–419, 1979.

J.A. Lewis et al., Integrated Control of Rhizoctonia Fruit Rot of Cucumber, The American Phytopathological Society, vol. 70, No. 2, pp. 85–89, 1980.

* cited by examiner

*Primary Examiner*—Francisco Prats
*Assistant Examiner*—Rosanne Kosson
(74) *Attorney, Agent, or Firm*—John D. Fado; Randall E. Deck

(57) ABSTRACT

Disease in plants caused by infection with cercosporin producing strains of *Cercospora* may be controlled by application of laccase. When applied to the locus of the plant, or parts or seed thereof, the cercosporin toxin produced by this pathogen is degraded by the enzyme, thereby preventing or minimizing damage to the plant. The laccase may be applied alone, or in combination with one or more laccase-producing microorganisms.

13 Claims, No Drawings

DEGRADATION OF CERCOSPORIN BY LACCASE

BACKGROUND OF THE INVENTION

1. Field of the Invention

This invention relates to a process for controlling disease in plants due to infection with cercosporin-producing strains of *Cercospora*.

2. Description of the Prior Art

Species of the fungus genus *Cercospora* are widespread, airborne pathogens afflicting a wide variety of agronomically important plants and crops. Spores of *Cercospora* which have landed on a plant germinate on the leaf surface and ultimately enter the leaf. The fungal mycelium then kills leaf cells, causing severe blighting of the leaf tissue.

Toxin production, particularly the production of cercosporin, plays an essential role in the pathogenicity of *Cercospora*. At least two types of toxin, beticolin and cercosporin, are produced by *Cercospora beticola*. Beticolin was reported to be produced by *C. beticola* (Schlösser, 1961, Phytopathol. Zeitschrift., 44:295–312) and presents a broad-spectrum of cytotoxic effects (Goudet et al., 1999, Biophys. J., 77:3052–3059). The second toxin, cercosporin, is a broad-spectrum photosensitizing perylene quinone toxin that is produced by members of the genus *Cercospora* and shows broad toxic activity against wide range of organisms that includes fungi (Chung et al., 1999, Mol. Gen. Genetics, 262:382–389), non-host plants, viruses, bacteria, and animal cell cultures. The structure of cercosporin produced by *Cercospora kikuchii* Gardner was determined independently by Lousberg et al. (1971, J. Chem. Soc. Chem. Commun., 1971:1463–1464) and Yamazaki et al. (1972, Agric. Biol. Chem., Volume 36, 1707–1718), as 1, 12-bis(2-hydroxypropyl)-2,11 dimethoxy-6,7-methylenedioxy-4,9-dihydroxyperylene3, 10-quinone (molecular weight: 534).

Once infection has been initiated, *Cercospora* produces cercosporin, which in the presence of light, is photoactivated and reacts with oxygen to produce the highly toxic superoxide anion ($O_2.^-$) and singlet oxygen ($^1O_2$) in the host plant. The singlet oxygen so produced, which is also the predominant species, acts to disrupt cell membranes (Daub, 1982, Plant Physiol., 69:1361–1364). Indeed, cercosporin has been reported to cause peroxidation of membrane fatty acids that leads to rupture of a plant plasma membranes and cell death. Daub and Briggs (1983, Plant Physiol., 71:763–766) suggested that break down of the host plant cell membrane by cercosporin provides *Cercospora* with nutrients required for growth and sporulation. We observed cercosporin in newly produced hyphal strands from mycelial plugs that were transferred two day earlier to fresh PDA plates. Observation of cercosporin in young hyphae is consistent with its role in obtaining nutrients from the host. For survival, cercosporin must be produced early after infection to obtain nutrient from the host. This observation is consistent with previously reported observations (Daub et al., 1992, Proc. Natl. Acad. Sci. USA, 89:9588–9592).

Leaf spot caused by *Cercospora beticola* Sacc. is one of the most important diseases of sugar beets (*Beta vulgaris* L.). The disease has been reported wherever sugar beet is grown (Bleiholder and Weltzien, 1972, Phytopathol. Zeitschrift., 73:93–114) and results in significant root yield loss and reduced sugar content of beets (Shane and Teng, 1992, Plant Dis., 76:812–820; Smith and Ruppel, 1971, Phytopathology, 61:1486–1487). Gross losses reach as high as 30% even in conditions wherein the disease severity is rated at 3 on a scale of 0–10 (Shane and Teng, 1992). Besides cultural practices and use of resistant varieties, control of *Cercospora* leaf spot has relied significantly on the use of several different fungicides (Windels et al., 1998, Plant Dis., 82:716–725). While applications of fungicides have proved effective in the management *Cercospora* leaf spot, rapid development of resistance by *C. beticola* against several of the fungicides has presaged the need for an alternate management strategy, such as biological control. Recently, the isolation of a Dtox gene from cercosporin-resistant microbes and the transformation of plants therewith has been described by Robeson et al. (U.S. Pat. No. 5,262,306). Daub et al. (U.S. Pat. No. 6,063,987) described the transformation of plants with a fungal gene encoding a protein conferring resistance to cercosporin. Upchurch et al. (U.S. Pat. No. 6,077,995) disclosed the production of transformed plants which exhibited increased resistance to cercosporin toxin by making the plant incapable of moving the toxin across its plasma cell membranes.

Several soil-inhabiting fungal agents, including *Laetisaria arvalis*, have been described for the control of variety of pathogens in different crops (Lartey et al., 1994, Soil Biol. Biochem., 26;81–88; Lartey et al., 1991, J. Phytopathology, 133;89–98). The Basidiomycete *L. arvalis* was first isolated from sugar beet residues in the soil by Boosalis in Nebraska in 1960 and was initially referred to as *Corticium*. sensu lato (Burdsall et al., 1980, Mycologia, 72:728–736; Hoch and Fuller, 1977, Arch. Microbiol., 11:207–224; Odvody et al., 1977, Biological control of *Rhizoctonia solani*, IN: Proc. Am. Phytopathol. Soc.), but was later placed in the genus *Laetisaria* by Burdsall et al. (Burdsall et al., 1980, ibid). L. arvalis has since been shown to have biocontrol activity over several plant seed and soil-borne pathogens, including \**Rhizoctonia solani, Pythium ultimumn*, and *Phoma* species when applied as a seed coating or as a soil amendment. *L. arvalis* has been examined for protection of a variety of agronomically important crops from these soil pathogens, including sugar beets, table beets, cucumbers, beans, soybeans, and turfgrass, by Hoch and Abawi (1979, ibid), Lewis and Papavizas (1980, Phytopathology, 70:85–89), Odvody et al. (1980, Phytopathology, 70:655–658), Allen et al. (1982, Mycol. Soc. Am. Newsletter, 33:34), Larsen et al. (1985, Plant Dis., 69:347–350), Martin et al. (1984, Phytopathology, 74:1092–1096), Conway et al. (1997, Plant Dis., 81), Gupta et al. (1999, J. Phytopathology, 147:19–24), and Conway et al. (2000, Proc. Okla. Acad. Sci., 80:39–46).

However, despite these advances, there is a persistent need for improved biocontrol agents for protecting plants from the effects of infection with *Cercospora*.

SUMMARY OF THE INVENTION

We have now discovered that disease in plants caused by infection with cercosporin producing strains of *Cercospora* may be controlled by application of laccase. When applied to the locus of the plant, or parts or seed thereof, the cercosporin toxin produced by this pathogen is degraded by the enzyme, thereby preventing or minimizing damage to the plant. The laccase may be applied alone, or in combination with one or more laccase-producing microorganisms.

In accordance with this discovery, it is an object of this invention to provide an improved process for controlling the development of disease in plants by cercosporin producing strains of *Cercospora*.

A further object of this invention is to provide an improved process for protecting a variety of agronomically important plants, including sugar beets, against disease by cercosporin producing strains of *Cercospora*.

Another object of this invention is to provide an improved process for protecting plants by detoxifying the toxin cercosporin produced by *Cercospora* species.

Yet another object of this invention is to provide an improved process for protecting plants against infection by cercosporin-producing species of *Cercospora* which does not require the use of fungicides.

other objects and advantages of this invention will become readily apparent from the ensuing description.

DETAILED DESCRIPTION OF THE INVENTION

The process of the invention is effective for protecting plants against disease development caused by any cercosporin producing species of *Cercospora*. Examples of specific, known cercosporin-producing species which the process. is effective against, as well as some of the diseases and host plants which are attacked by the fungus and which may be protected by this invention, include but are not limited to:

*Cercospora apii*, (garden carrot), early blight (celery),
*C. arachidicola*, (peanut),
*C. ariminiensis*,
*C. asparagi*, leaf spot (asparagus),
*C. bertoreae*,
*C. beticola, Cercospora* leaf spot (sugar beet, spinach),
*C. bizzozeriana*,
*C. bolleana*, leaf spot (fig),
*C. brassicicola*, leaf spot (broccoli, cauliflower, cabbage),
*C. canescens*, leaf pod spot (hyacinth bean),
*C. capsici*, leaf spot (sweet pepper),
*C. caribaea*, white leaf spot (cassava),
*C. carotae, Cercospora* leaf blight (carrot),
*C. chenopodii*,
*C. circumscissa*, (prune),
*C. cistinearum*,
*C. citrullina, Cercospora* leaf spot (watermelon), leaf spot (cucumber),
*C. cladosporioides*,
*C. clavata, Cercospora* leaf spot (turfgrass),
*C. coffeicola*, leaf spot (coffee),
*C. colocasiae, Cercospora* leaf spot (taro),
*C. columnaris, Cercospora* leaf blight (carrot),
*C. cruciferarum*,
*C. cruenta*, leaf spot (garden bean, asparagus bean),
*C. depazoides*,
*C. desmodii*,
*C. diazu*,
*C. diospryi*,
*C. dubia*,
*C. dulcamarae*,
*C. elaeochroma*,
*C. elongata*,
*C. erysimi*,
*C. fiagellaris*,
*C. fusimulcans, Cercospora* leaf spot (turfgrass),
*C. fragariae*, leaf spot (strawberry),
*C. gentianae*,
*C. granuliformis*, (*Viola* sp.),
*C. graphioides*, (prune),
*C. grisea*,
*C. hayii*,
*C. kalmiae*, (rhododendron)
*C. kikuchii, Cercospora* leaf spot and purple leaf stain (soybean),
*C. koepkei*, yellow spot (sugar cane),
*C. longipes*, brown spot (sugar cane),
*C. longissima*, leaf spot (lettuce),
*C. malayensis*, leaf spot (hibiscus),
*C. mali*, leaf spot (pear),
*C. malvacearum*,
*C. malvicola*,
*C. mamaonis*, leaf and fruit spot (papaya),
*C. medicaginis, Cercospora* leaf spot (alfalfa),
*C. melanochaeta*,
*C. melongenae*, leaf spot (eggplant),
*C. menispermi*,
*C. musae*, leaf spot (banana),
*C. nasturtii*, leaf spot (watercress),
*C. nerii-indica*, leaf spot (oleander),
*C. nicotianae*, frog-eye spot (tobacco),
*C. oryzae*, (rice),
*C. papayae, Cercospora* black leaf spot (papaya),
*C. personata*, (peanut)
*C. penniseti, Cercospora* leaf spot (pearl millet),
*C. petroselini*, leaf spot (parsley),
*C. plantaginis*, leaf spot (*Plantago* sp.),
*C. polygonorum*,
*C. prenanthis*,
*C. punicae*, (pomegranate),
*C. purpurea*, leaf spot (avacado),
*C. resedae*,
*C. rhoina*,
*C. ricinella*,
*C. rosicola*,
*C. sacchari*, (sugar cane),
*C. rubi*,
*C. sequoiae var. juniperi, Cercospora* needle blight (juniper and cedar), needle spot (Portugese cypress),
*C. setariae*,
*C. sojina*, leaf spot (soybean),
*C. tectoniae*, leaf spot (teak),
*C. thujina*, needle spot (Portugese cypress),
*C. unamunoi*,
*C. vaginae*, red spot or leaf-sheath spot (sugar cane),
*C. violae*, (*Viola* sp.)
*C. zeae-maydis*, gray leaf spot (maize), and
*C. zebrine*, leaf spot (alfalfa, sweet clover).

Still other non-limiting examples of plants which may be protected against disease caused by cercosporin-producing species of *Cercospora* include taro, coffee, sorghum, and numerous ornamental flowers.

Laccase (E.C. 1.10.3.2) is produced by a number of different plants, bacteria, and fungi. The particular source of the laccase is not critical, and enzyme suitable for use herein may be obtained commercially, or it may be recovered from plant material, or produced by bacterial or fungal fermentation. Preferred laccases used herein include the fungal laccases produced by *Pleurotus ostreatus, Trametes versicolor*, and *Laetisaria arvalis*. Without being limited thereto, examples of other laccases which may be used herein include fungal laccase produced by *Pycnoporus sanguineus, Phlebia radiata, Agaricus campestis, Russula delica, Marasmius quercophilus, Pycnoporus sanguineus, Gonoderma lucidum, Gaeumannomyces graminis* var. *graminis, Aspergillus nidulans, Podospora* species, *Botrytis* species, *Collybia* species, *Fomes* species, *Lentinus* species, *Polyporus* species, *Rhizoctonia* species, *Myceliophthora thermophila, Polyporus pinsitus, Pyricularia oryzae, Neurospora* species, and *Fusarium proliferatum*, and bacterial laccase from *Azospirillum lipoferum*.

Production of laccase from the preferred fungi *Pleurotus ostreatus, Trametes versicolor*, or *Laetisaria arvalis* may be accomplished by conventional culture techniques under aerobic conditions that are effective to promote growth. Any number of well-known liquid or solid culture media may be used, although growth on liquid media (with or without agitation) is preferred as the enzyme is secreted into the media and recovery is simplified. Without being limited thereto, one preferred culture media is potato dextrose broth. Examples of other suitable media include conventional mycology culture media such as Rawlin Thom medium, sabouraud dextrose broth, brain-heart infusion broth, malt extract broth, or 5% ground wheat bran or millet with 1% peat moss. The fungi will typically grow and produce laccase over relatively wide pH and temperature ranges, generally between about 2.0 to 7.5 and 150 to 28° C., respectively. The optimum conditions selected will of course vary with the particular fungus selected and may be readily determined.

Under cultivation conditions, laccase is produced concurrently with growth. Once a sufficiently heavy growth of the fungus has been obtained, the soluble laccase may be separated or recovered from the cells using techniques conventional in the art, such as by centrifugation or filtration. As a practical matter, it is envisioned that commercial formulations of laccase may be prepared directly from the crude extracts of the liquid culture medium from which cells have been removed, thereby obviating the need for further purification.

Optionally, the laccase remaining in the culture medium may be further concentrated and purified, particularly for applications demanding a high degree of purity where contamination by other microbial products or culture media components may be undesirable. Suitable techniques for concentration and/or purification of the laccase may be readily determined by the practitioner skilled in the art and include, for example, ultrafiltration, dialysis, ion-exchange chromatography, and HPLC size-exclusion chromatography, affinity chromatography, and electrophoresis. Using these techniques, the laccase may be recovered in pure or substantially pure form.

The laccase, whether in purified form or contained in the crude, cell-free extracts of culture media, may be formulated in conjunction with a suitable solid or liquid inert carrier or vehicle as known in the art. The skilled practitioner will recognize that such carriers must be compatible with the enzyme, and should also be agronomically acceptable. For purified or substantially purified laccase, renaturation buffer and water are preferred liquid carriers. The laccase may also be formulated with solid inert carriers such as talc, clay or vermiculite. In a first preferred embodiment, liquid cell-free extracts of the culture medium are preferably applied directly upon or to the locus of the plant or its parts or seed to be treated. Alternatively, in a second preferred embodiment, the water is removed from these crude extracts to partial or substantial dryness, and the resultant dried mixture broken up or ground into small particles using techniques conventional in the art. Without being limited thereto, suitable water removal techniques include air drying, evaporation or filtration.

Granules of the crude or purified laccase may be contacted with an optional, preferred sticking agent or adherent as are known in the art to facilitate adherence of the granular product to a target plant or part thereof to be treated. Suitable sticking agents may be readily determined by the skilled practitioner and include but are not limited to latex (RHOPLEX B-15, Rohm and Haas, Philadelphia, Pa.), sugars such as sucrose, glucose, fructose, mannose, α-methyl glucoside or corn syrup (as described by Shasha and McGuire, U.S. Pat. No. 5,061,697, issued Oct. 29, 1991, the contents of which are incorporated by reference herein), alginate, methylcellulose, and OPADRY (Colorcon, Inc., Westpoint, Pa.).

In an alternative embodiment, controlled release of the laccase may be accomplished by encapsulation within an inert carrier using conventional techniques. Suitable carriers of this type include but are not limited to alginate gels, wheat-gluten, matrices, starch matrices, or synthetic polymers as are known in the art.

Besides the laccase, other additives and adjuncts may be formulated into the biocontrol composition. Examples of these include stabilizers such as sucrose, an alkali metal hydrogen phosphate salt, glutamate, gelatin, or casein, inert fillers, UV protectants such as Congo-red, folic acid, paraminobenzoic acid or azobenzene, fertilizers, and pesticides. Particularly preferred for inclusion are fungicides. Without being limited thereto, suitable fungicides include those which are commonly used for controlling *Cercospora* disease, such as benzimidazoles, sterol biosynthesis inhibitors (e.g., tetraconazole), or stobilurin fungicides.

In an alternative, yet preferred embodiment, the laccase may be applied in conjunction with viable microbial cells of a known laccase producer. Although laccase is stable and remains effective for cercosporin degradation over an extended period of time, this embodiment provides the dual advantage of providing both immediate degradation of cercosporin toxin, as well as protection over a greater, more prolonged period of time. Any one or more of the above-mentioned laccase producers which are non-pathogens may be used herein. Further, the microorganism may be the same as or different from the microorganism used to prepare the laccase. Generally, use of *Pleurotus ostreatus* or *Trametes versicolor* is preferred, with use of *Laetisaria arvalis* being particularly preferred. These microorganisms may be formulated together or separately from the laccase composition, and may be applied at the same or different time as the laccase composition.

To be effective, the laccase (either alone or in combination with the above-mentioned laccase-producing microorganisms), must be applied to the locus of, or in the vicinity of, the plant, its parts, or seed to be protected. In one preferred embodiment, the laccase is applied directly onto the plant, particularly onto the foliage. In another preferred embodiment, the laccase may be applied onto parts of the plant, such as the harvested fruit, roots, or vegetables after they have been removed from the plant. This embodiment is particularly preferred for the protection of harvested beets and carrots. Alternatively, because *Cercospora* are native to the soil, the laccase may also be applied to the soil in the locus or vicinity of the plant or its seed or, in the case of greenhouse plants, added to potting mix of plants grown in greenhouse conditions. Compositions of the laccase will typically be applied by spraying or dusting.

The subject laccase acts to prevent disease or reduce disease severity caused by cercosporin-producing species of *Cercospora* on a treated plant or its parts, relative to untreated controls. Application of the laccase to plants, their parts, or to the soil in their vicinity, degrades the cercosporin toxin which is produced by *Cercospora*, reducing or eliminating its toxicity. Without wishing to be bound by theory, this detoxification of the cercosporin prevents or significantly reduces production of superoxide anion and singlet oxygen thereby, and thus reduces the disruption of the host plant's cell walls and membranes. Furthermore, the mycelia of the *Cercospora* are less able to penetrate or disrupt the intact or undamaged host plant cell walls, depriving the fungus of nutrients and preventing or significantly reducing its growth and sporulation.

Accordingly, the laccase should be applied in an amount effective to degrade cercosporin toxin on the subject plant, its parts, or in the soil in the vicinity of the plant. An "effective amount" of the laccase is therefore defined herein as those quantities of laccase that will result in a significant decrease in the concentration of active cercosporin toxin on the subject plant, its parts, or in the soil in the vicinity of the plant as compared to an untreated control. Because the ultimate goal is the protection of plants or their parts from infection, a reduction in the concentration of active cercosporin toxin may be demonstrated by a significant reduction in the incidence or severity of disease caused by cercosporin-producing *Cercospora* on the subject plant or its parts as compared to untreated control, plants. Alternatively or in addition, degradation of cercosporin may also be measured using a variety of conventional techniques, such as spectrophotometry as described in Example 1 hereinbelow or thin-layer chromatography as described by Robeson et al. (U.S. Pat. No. 5,262,306, the contents of which are incorporated by reference herein), or by a significant reduction in toxicity toward cultures cercosporin-sensitive microorganisms. The actual effective amount will vary with the host plant, the concentration of *Cercospora* pathogens in the vicinity of the host plant, the source of the laccase, the method of treatment (e.g., foliar spray or soil treatment), and environmental conditions, and may be readily determined by the practitioner skilled in the art. For example, commercially available laccase is typically effective for the degradation of cercosporin at a range between about 25–50 Units laccase per 25–50 mg of toxin. However, some fungal laccases, such as those from *Pleurotus ostreatus* or *Laetisaria arvalis*, appear to possess greater activity against the toxin and thus the effective amount when using those laccases may be lower. Without being limited thereto, the generally preferred amounts for application of laccase such as from *Pleurotus ostreatus* onto the foliage of a field crop such as sugar beets, maize, or soybeans, are greater than or equal to about 5,000 Units of laccase per acre treated, and less than or equal to about 20,000 Units of laccase per acre.

The following examples are intended only to further illustrate the invention and are not intended to limit the scope of the invention which is defined by the claims.

EXAMPLE 1

Materials and Methods

Microorganisms and Culture Conditions

*Cercospora beticola* Sacc. isolate C2 (Whitney et al., 1976, Phytopathology, 66:1158–1160) was provided by John J. Weiland, USDA, Fargo, N.Dak. and isolate S2 was isolated from sugar beet fields at Sidney, MT, and was provided by Anthony J. Caesar, USDA, Sidney, MT. Both isolates of *C. beticola* were cultured on potato dextrose agar (PDA, DIFCO Laboratories), at 23° C. with a 5 hr photoperiod (light source was fluorescent light with an intensity of 45 $\mu$mol m·2s·1) for maximum production of cercosporin. Three week-old cultures were used for extraction of cercosporin.

Cercosporin Extraction

Cercosporin is visible as a red pigment on the underside of cultures growing on agar medium. Cercosporin was extracted following a modified procedure of Daub (1982, ibid). Briefly, the agar containing the fungal mycelia was removed and placed on plastic screens in a laminar flow hood to allow them to dry for 2–3 days. Dried cultures were ground up in a blender, and then 50 g of materials were extracted in 300 ml ethyl acetate with agitation for 1 hr. After decanting the solvent, the procedure was repeated until no more red color came from the mycelia. The solvent was evaporated off in a rotary evaporator to dryness. The dry residue was brought up to in a small volume of chloroform. A small amount of pentane was added to the mixture and the extracted material was put in the freezer (at least one-week) until crystals formed. The liquid was then decanted and a small amount of pentane was used to wash the crystals. The crystallization process was repeated to purify the cercosporin. For control, purified cercosporin from *Cercospora hayii* (Sigma) was used.

Enzymes

Laccase from *Pleurotus ostreatus* and *Tremetes versicolor* were purchased at Trienzyme, Inc. (Canada).

Enzymatic Degradation

Cercosporin crystals extracted from the isolates C2 and S2 of *Cercospora beticola* and purified cercosporin from *Cercospora* hayii (Sigma) were dissolved at 1 mg/ml in 100% ethanol and used as stock solutions. The enzymatic reaction consists cercosporin at the concentration of 25 $\mu$g/ml in 20 mM of MOPS (Morpholinopropane sulforic acid, Sigma) buffer, pH 6, and 50 units/ml of laccase from *P. ostreatus* and *T. versicolor*. Experiments were carried at 25° C. and in the dark to prevent photooxidation of cercosporin. Enzymes were stored in a −20 freezer. Controls were treated the same way as laccase-treated samples except no laccase was added to the reaction.

A Perkin-Elmer Lamda 20 spectrophotometer was used for the spectrophotometric assay. Absorbence of cercosporin was monitored from 200 nm to 600 nm. The speed of scanning was 960 nm/minutes. The results shown are from one experiment typical of three.

Test of detoxification of cercosporin in culture plate

Two milliliters of P. ostreatus and *T. versicolor* laccase (100 units/ml in 20 mM MOPS buffer, pH 6, Sigma) was added to cercosporin producing 3 week-old *C. beticola* cultures growing in PDA. Culture plates were rotated by hand until the enzyme solution was completely absorbed in the agar. The plates were incubated for 24 hr at 23° C. with a 5 hr photoperiod (light source was fluorescent light with an intensity of 45 mmol m·2s· 1). Then they were opened and exposed to the environment on the lab bench for 6 hr to contaminate the cultures with air-borne microorganisms. An additional 48 hr to 72 hr of incubation in the incubator with the light source was followed until visible propagation of the air-borne microorganisms. Control cultures of cercosporin producing *C. beticola* received the buffer alone without laccase and they were treated the same way than cultures treated with laccase. Experiments were repeated 3 times.

Results and Discussion

The deep red color of cercosporin produced extracellularly by 3 week-old cultures of *C. beticola* (isolate C2) in PDA turned clear in the presence of *P.ostreatus* and *T. versicolor* laccase. When cultures plates were exposed to ambient air, plates with laccase showed growth of air borne microorganisms after 48–72 hr while plates without laccase did not. This suggests that laccase has degraded and detoxified cercosporin which no longer is toxic to microorganisms.

The maximum absorption at 220, 279, and 480 nm exhibited by cercosporin from *C. hayii* and *C. beticola* (C2 and S2) was in agreement with spectra reported previously by Yamazaki and Ogawa (1972) in their study of the chemistry and stereochemistry of cercosporin from *C. kikuchii*.

Laccase from both *P. ostreatus* and *T. versicolor* effected cercosporin extracted from *C. hayii* and from *C. beticola* (C1 and S2). A color change over 10 minutes of reaction was noted from deep red to light pink for the 3 sources of cercosporin when treated with either *P. ostreatus* or *T. versicolor* laccase. Spectrophotometric data showed a decrease in absorbence around 220, 279 and 490 nm in the 3 different cercosporin treated with the two laccases. Non-treated samples exhibited no or little change in absorbence at the three wavelengths. At 480 nm, a peak shift of 10 nm was recorded for *C. hayii* cercosporin, 21 nm for C2 cercosporin, and 10 nm for S2 cercosporin, after 10 minutes of treatment with *P. ostreatus* laccase. When treated with *T. versicolor* laccase, *C. hayii* cercosporin displayed a peak shift of 20 nm at 480 nm, and there were no more peaks detected with C2 and S2 cercosporin. These data suggested that cercosporin is degraded over time in the presence of laccase, regardless of the species of *Cercospora*. Cercosporin may undergo ring-opening oxidation by laccase.

The method of Daub et al. (1992, ibid) was used to detect cercosporin. Cercosporin was excited with a 488 nm excitation filter and its fluorescence was detected at >605 nm using a Zeiss 410 confocal scanning laser microscope. Images of hyphae from a 3 week-old *C. beticola* (C2) culture showed no fluorescence when the culture was challenged for 24 hr with the *P. ostreatus*, whereas the control culture without *P. ostreatus* fluoresced. This suggests that *P. ostreatus* released a chemical compound in the medium that degrades cercosporin.

It is understood that the foregoing detailed description is given merely by way of illustration and that modifications and variations may be made therein without departing from the spirit and scope of the invention.

We claim:

1. A method for controlling disease in plants caused by infection with cercosporin producing species of *Cercospora* comprising applying a cercosporin-degrading effective amount of a composition comprising laccase to a plant or parts thereof, wherein said composition comprises a substantially cell-free extract recovered from a laccase producing organism, and further applying a cercosporin-degrading effective amount of a laccase-producing microorganism to the locus of said plant or seed of said plant, wherein said laccase-producing microorganism is selected from the group consisting of *Laetisaria* species and *Pleurotus* species.

2. The method of claim 1 wherein said composition comprises substantially pure laccase.

3. The method of claim 1 wherein said composition comprises a cell-free extract recovered from a laccase producing organism.

4. The method of claim 3 wherein said laccase producing organism is a first microorganism selected from the group consisting of bacteria and fungi, and said composition comprises a culture medium produced by a culture of said first microorganism and which is free of cells of said first microorganism.

5. The method of claim 1 wherein said plant is selected from the group consisting of sugar beets, carrots, soybeans, Juniper trees, Cedar trees, turfgrasses, alfalfa, watermelon, pearl millet, papaya, maize, celery, prunes, and rhododendrons.

6. The method of claim 5 wherein said plant is a sugar beet.

7. The method of claim 1 wherein said composition is applied onto the foliage of said plant.

8. The method of claim 1 wherein said composition is applied onto the harvested root of said plant.

9. The method of claim 8 wherein said root of said plant is selected from the group consisting of sugar beets and carrots.

10. The method of claim 1 wherein said laccase-producing microorganism is applied onto the soil in the vicinity of said plant or seed thereof.

11. The method of claim 1 wherein said laccase-producing microorganism is *Laetisaria arvalis*.

12. The method of claim 1 wherein laccase is applied to a field crop in an amount greater than or equal to about 5,000 Units of laccase per acre.

13. The method of claim 12 wherein laccase is applied to a field crop in an amount greater than or equal to about 5,000 Units of laccase per acre, and less than or equal to about 20,000 Units of laccase per acre.

* * * * *